United States Patent [19]
Elkouby

[11] Patent Number: 5,795,149
[45] Date of Patent: Aug. 18, 1998

[54] DEVICE FOR ATTACHING AN ORTHODONTIC UNIT AND AN ORTHODONTIC UNIT INCORPORATING SUCH DEVICE

[75] Inventor: Charles Eric Elkouby, Paris, France

[73] Assignee: AIDA International, Montreuil, France

[21] Appl. No.: 676,111

[22] PCT Filed: Dec. 29, 1994

[86] PCT No.: PCT/FR94/01551

§ 371 Date: Jul. 10, 1996

§ 102(e) Date: Jul. 10, 1996

[87] PCT Pub. No.: WO95/18578

PCT Pub. Date: Jul. 13, 1995

[30] Foreign Application Priority Data

Jan. 11, 1994 [FR] France .................. 94 00187

[51] Int. Cl.[6] ................................. A61C 7/00
[52] U.S. Cl. ........................................... 433/5
[58] Field of Search ............................... 433/5

[56] References Cited

U.S. PATENT DOCUMENTS

| | | | |
|---|---|---|---|
| 4,226,589 | 10/1980 | Klein | 433/5 |
| 4,392,825 | 7/1983 | De Woskin | 433/5 |
| 4,427,380 | 1/1984 | Carter et al. | 433/5 |
| 4,600,382 | 7/1986 | Förster | 433/5 |
| 4,734,032 | 3/1988 | DeWoskin | 433/5 |

FOREIGN PATENT DOCUMENTS 2706282 12/1994 France .
2706382 12/1994 France .

*Primary Examiner*—Robert P. Swiatek
*Attorney, Agent, or Firm*—Greenblum & Bernstein P.L.C.

[57] ABSTRACT

A device for attaching an orthodontic unit, and an orthodontic unit that incorporates such device, in which the unit is secured to a protective pad using a flexible buckle confining the median portion of a yoke. An arrangement is provided on the pad that limits pivoting of the unit in the plane of the pad. The unit is inserted under a band joined to the pad.

12 Claims, 1 Drawing Sheet

DEVICE FOR ATTACHING AN ORTHODONTIC UNIT AND AN ORTHODONTIC UNIT INCORPORATING SUCH DEVICE

BACKGROUND OF THE INVENTION

1. Field of the Invention

The present invention relates to a device for attaching an orthodontic unit and to an orthodontic unit that incorporates such device.

2. Description of Background and Relevant Information

In dentistry, one is led to exert a tensile force on a tooth. The equipment that is used comprises two portions: an endobuccal portion anchored on the tooth to be straightened, and an exobuccal portion, or traction unit, connected to the first and making it possible to exert a force on the tooth.

The traction unit is connected through one of its ends to the tooth to be straightened, and is fixed to the patient through its other end.

The portion that is fixed to the patient is constituted by a yoke-shaped element engaged through one of its arms in the unit body. If the tensile force exceeds a predetermined value, the yoke can escape from the unit body. Such a unit is described in the French patent application no. 93 07360, filed on Jun. 14, 1993 in the name of the applicant.

The yoke is fixed, through its median portion, on a protective pad. This pad can constitute a nape band or a portion of a headband. This pad is adapted to prevent the traction unit from injuring the patient.

As the aforementioned pad is made out of a padded textile material, the median portion of the yoke is confined in a buckle made of a textile material that ensures the attachment of the unit on said pad.

Experience has shown that the protective pad is not totally efficient in view of the fact that the traction unit, maintained on the pad through only one of its ends, is very free; it can pivot at this end and reach the patient's skin.

A prior solution consisting of increasing the surface of the pad does not make it possible to remedy this problem. Indeed, if the dimensions of the pad are increased, the cost thereof is increased in the same proportion. Moreover, if the cost-related problem is neglected, the aforementioned solution cannot be implemented in a satisfactory manner, because if the pad is too large, the latter causes a discomfort to the patient.

SUMMARY OF THE INVENTION

An object of the present invention, which remedies the aforementioned disadvantages, is to provide the protective pad with an arrangement that renders it possible to limit the pivoting of the traction unit.

BRIEF DESCRIPTION OF THE DRAWINGS

The present invention will be better understood along the following description, made in reference to the annexed drawing, provided by way of a non-limiting example only, in which.

DETAILED DESCRIPTION OF THE INVENTION

Figure 1:
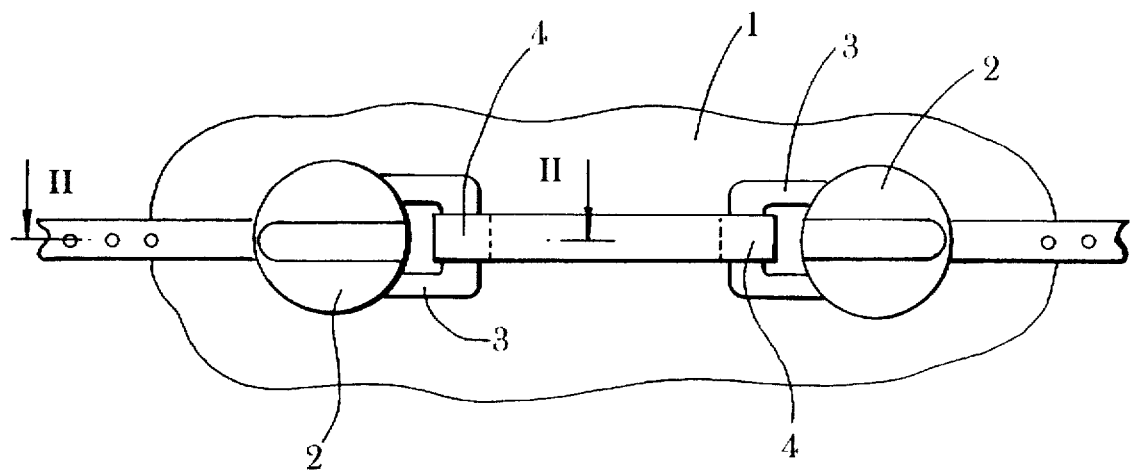
FIG. 1 shows a usual pad, used as a nape band, that includes its two traction units.

With reference to the drawing, pad 1 forms a nape band, on which two traction units of a known type are fixed. Each unit is formed by the association of two portions 2 and 3.

Figure 2:
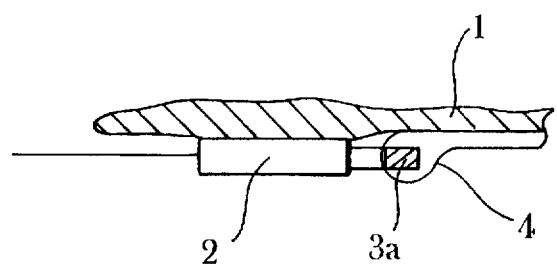
FIG. 2 is a cross-sectional view taken along the line II—II of FIG. 1, the unit body being uncut.
Figure 3:
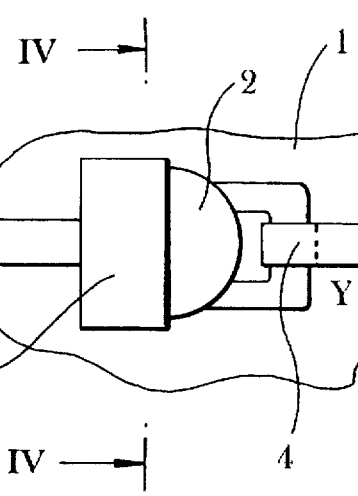
FIG. 3 is a view similar to FIG. 1, showing the implementation of the device of the invention.
Figure 4:
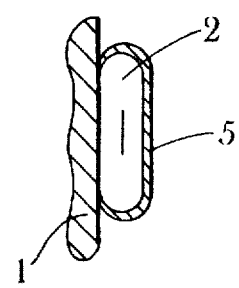
FIG. 4 is a cross-sectional view taken along the line IV—IV of FIG. 3, the unit body being uncut.

The portion 2 forms the unit body in which the yoke-shaped element 3 is engaged. Each unit is attached to the pad 1 by means of a buckle 4 confining the median portion 3a of the yoke (see FIG. 2), and made by means of a strip of fabric sewn on the pad 1, for example. If the value of the traction to which the unit is subjected exceeds a predetermined value, the two elements 2 and 3 separate from one another. This technique is well-known.

It appears from the foregoing description that the unit can pivot in the plane of the pad 1 and escape from its protective action. The detrimental effects of this displacement are increased when one uses more improved units, such as that described in the aforementioned French patent application, because their length is much greater than that of the unit shown in the drawing.

According to the invention, one remedies this disadvantage by providing on the pad 1 a means for limiting the pivoting of the unit.

According to an embodiment, the pad 1 has a band 5 under which the unit is engaged. This band is made from a strip of fabric sewn through its ends on the pad 1 and extending transversely to the longitudinal axis of the latter, defined by the line X–Y.

As the band 5 is made of a flexible material, the unit is not rigidly attached to the pad 1, and it can pivot in the plane of the pad, or upon the surface of the pad, without, however, escaping therefrom.

What is claimed:

1. In combination, an orthodontic traction unit and a device for attaching said orthodontic traction unit, wherein:
   said orthodontic traction unit comprises a unit body and a yoke;
   said device for attaching said orthodontic traction unit comprises:
   a protective pad defining a plane;
   a flexible buckle affixed to said pad, said flexible buckle and a median portion of said yoke of said traction unit forming a connection, said connection allowing said traction unit body to pivot within said plane of said pad with respect to said flexible buckle; and
   means affixed to said pad and affixed to said traction unit for limiting pivoting of said traction unit.

2. The combination according to claim 1, wherein said means comprises a band affixed to said pad.

3. The combination according to claim 2, wherein said band is made of a flexible material.

4. The combination according to claim 3, wherein said band is sewn to said pad, thereby being affixed thereto.

5. The combination according to claim 1, wherein said flexible buckle comprises opposite end portions, whereby said connection between said buckle and a median portion of said yoke of said traction unit is at one of said opposite end portions, and wherein a yoke of a second traction unit is connected to a second of said opposite end portions of said flexible buckle.

6. An orthodontic traction unit apparatus comprising:
   at least one orthodontic unit body and at least one yoke, said at least one yoke being secured to said at least one unit body, said at least one yoke having a median portion extending from said at least one unit body, said at least one unit body and said at least one yoke forming a traction unit;

a protective pad adapted to be positioned at a nape of a patient's neck, said pad defining a plane;

a flexible buckle affixed to said pad, said flexible buckle and said median portion of said at least one yoke forming a connection, said connection allowing said at least one unit body to pivot within said plane of said pad with respect to said flexible buckle; and means affixed to said pad and affixed to said traction unit for limiting pivoting of said traction unit.

7. An orthodontic traction unit apparatus according to claim 6, wherein said means comprises a band affixed to said pad.

8. An orthodontic traction unit apparatus according to claim 7, where said band is made of a flexible material.

9. An orthodontic traction unit apparatus according to claim 8, wherein said band is sewn to said pad, thereby being affixed thereto.

10. An orthodontic traction unit apparatus according to claim 6, wherein said flexible buckle comprises opposite end portions, whereby said connection between said buckle and a median portion of said at least one yoke of said traction unit is at one of said opposite end portions, and wherein a yoke of a second traction unit is connected to a second of said opposite end portions of said flexible buckle.

11. An orthodontic traction unit apparatus comprising:

at least two traction units, each traction unit comprising one orthodontic unit body and at least one yoke, said at least one yoke being secured to said unit body, said at least one yoke having a median portion extending from said unit body;

a protective pad having an inner surface adapted to be positioned against a nape of a patient's neck, said pad further having an outer surface;

a flexible buckle affixed to said outer surface of said pad, said flexible buckle having spaced portions for securing respective median portions of yokes of said at least two traction units, said flexible buckle and respective median portions of associated yokes forming respective connections, each connection allowing a respective traction unit to pivot with respect to said protective pad; and two devices affixed to said pad, each of said two devices connected to a respective traction unit to confine pivoting of said respective traction unit within a periphery of said outer surface of said protective pad.

12. An orthodontic traction unit apparatus according to claim 11, wherein each of said two devices affixed to said pad to confine said pivoting of said traction units comprises a flexible band inside which a respective unit body is secured.

* * * * *